United States Patent [19]

Eckles

[11] Patent Number: 4,803,370

[45] Date of Patent: Feb. 7, 1989

[54] INFRARED LIGHT GENERATION

[75] Inventor: Robert D. Eckles, Malcolm, Nebr.

[73] Assignee: Li-Cor, Inc., Lincoln, Nebr.

[21] Appl. No.: 50,878

[22] Filed: May 18, 1987

[51] Int. Cl.$^4$ .............................................. G01N 21/35
[52] U.S. Cl. ............................ 250/504 R; 250/493.1; 250/343; 219/548
[58] Field of Search ............. 250/504 R, 495.1, 493.1, 250/343; 313/548, 547; 219/548

[56] References Cited

U.S. PATENT DOCUMENTS

| | | | |
|---|---|---|---|
| 3,473,022 | 10/1969 | Walz et al. | 250/343 |
| 4,310,781 | 1/1987 | Steinhage et al. | 313/547 |
| 4,480,191 | 10/1984 | Karpowycz | 250/343 |

*Primary Examiner*—Bruce C. Anderson
*Assistant Examiner*—Jack I. Berman
*Attorney, Agent, or Firm*—Vincent L. Carney

[57] ABSTRACT

To measure the amount of carbon dioxide in a mixture of gases, a source of infrared light includes a porous getter emitted formed of an inner tungsten heater with a layer of sintered together zirconium and carbon powder covered with spectrographic grade carbon over at least 50 percent of its surface serving as a getter and an emitter of infrared light. It is mounted within a vacuum and emits light in a strong spectrum including light having a bandwidth of at least 150 nanometers with a center point of substantially 4.2 micrometers. The light is transmitted through reference and sample flow cells each including a corresponding one of a reference gas and a sample gas onto a photosensor. The light source includes a reflector located within a range of no more than 1 centimeter from the emitter getter for reflecting heat back to said emitter getter at least 50 percent of its surface and has a window aligned with said infrared light sensor with an opening of area of between 0.05 to 20 square millimeters. The heater heats the emitter getter to a temperature in the range of 600K to 2,000K.

72 Claims, 2 Drawing Sheets

INFRARED LIGHT GENERATION

BACKGROUND OF THE INVENTION

This invention relates to the generation of infrared light and more particularly to the generation of infrared light for use in instruments, such as for example, carbon dioxide analyzers.

It is known to measure the amount of carbon dioxide in a mixture of gases by detecting the amount of infrared light that is absorbed. This light is generated by heating elements to a temperature in which emission in the infrared spectrum is particularly efficient.

One type of infrared emitter is a metal which: (1) can be heated to a temperature causing efficient emission of infrared light; and (2) is embedded in or coated with an insulator. Such emitters are expensive and subject to burning out because of the low heat conductivity of the coating.

Another prior art type of infrared emitter consists of a substance which is mounted in a vacuum and heated to a temperature at which efficient infrared radiation occurs. Such arrangements have a disadvantage in that the heated element deteriorates with time because of gases within the vacuum chamber. Such gases slowly accumulate across a period of time until they have a deleterious effect on the element.

One technique for prolonging the life of vacuum mounted infrared elements is to include a getter within the vacuum container to remove gases. One type of getter is an evaporable getter. This type of getter has the disadvantage of eventually coating the vacuum container and thus reducing the light-emission efficiency.

Another type of getter is a non-evaporable getter. This type of getter has a disadvantage in that it is either unheated and thus slow in its activity or is heated, and in time, becomes inactive. If it is heated to maintain its activity, energy must be expended which causes a drain on batteries.

SUMMARY OF THE INVENTION

Accordingly, it is an object of the invention to provide a novel infrared source.

It is a further object of the invention to provide a novel technique for generating infrared light.

It is a still further object of the invention to provide a novel method and apparatus for emitting infrared light over a long period of time.

It is a still further object of the invention to provide a technique and apparatus for efficiently emitting infrared light with a sufficiently low power drain to be advantageous for use in portable instruments.

It is a still further object of the invention to provide an efficient carbon dioxide analyzer with low power drain and long life.

It is a still further object of the invention to provide a novel portable photosynthesis analyzer in which the carbon dioxide analyzer has long life.

In accordance with the above and further objects of the invention, an infrared source is mounted within a carbon dioxide analyzer or other instrument to radiate infrared light through a sample. The light is detected and used to determine the amount of carbon dioxide in the sample. Such carbon dioxide analyzers are used in some photosynthesis meters.

To make an infrared source with low power drain and long life for use in portable instruments, a combined emitter getter is prepared. This combined emitter getter is formed with an electrical heating element as its central axis. A good but structurally weak infrared emitter is mixed with a powdered non-evaporating getter material and sintered together about the heater so that when the electrical heater is energized to generate heat, the infrared emitter is heated to give off infrared light and at the same time the getter material is heated to operate efficiently.

Advantageously, powdered zirconium may be used as the getter material and graphite as the efficient high-emissivity radiator of infrared light. The two may be mixed together and sintered to form a combined getter and infrared emitter. Spectrometer grade carbon is rubber over the surface so that at least 50 percent of the surface is covered, while preserving gas porosity so that the getter remains active.

In operation, the getter emitter is heated in a vacuum to a temperature in which the getter has long life and efficient getter action in removing gases while at the same time the high infrared emissivity material emits infrared radiation efficiently.

The combined unit has an emissivity of at least 60 percent and a size occupying a volume of between 0.01 cubic millimeters to 100.0 cubic millimeters. Advantageously, it is mounted within a heat reflector designed to focus heat back upon it and has a window with an open area of at least 0.7 square millimeters. The reflective surface of the heat reflector is mounted so that at least 50 percent of it is, at its closest distance, no more than 1 centimeter from the surface of the emitter getter. This unit transmits infrared light through a window which has low attenuation of infrared light and sufficient physical strength to preserve the vacuum.

In using the light source of this invention, current is applied to the heater element in the center of the getter emitter so that it is heated to a temperature of between 600 K. to 2,000 K. The high infrared emissivity material emits infrared radiation across a bandwidth of at least 1,500 nanometers which encompasses within it light having a wavelength of 4.2 microns.

Advantageously, approximately 3 amperes are applied through a 1 ohm resistance heater and the temperature is maintained at approximately 1,000 degrees K. The high emissivity material is carbon and the getter is zirconium which, at the same temperature, maintains activity for an unexpectedly long period of time, thus preserving the life of the infrared lamp for an unexpectedly long time.

From the above description, it can be understood that the infrared light source of this invention has several advantages such as: (1) it has long life; (2) it has good structural strength; (3) it is economical to manufacture even though it uses a material that is not structurally strong as the infrared radiating material; (4) it is efficient in its use of electrical power and thus particularly suitable for portable instruments; and (5) it combines good getter activity with high infrared emissivity.

SUMMARY OF THE DRAWINGS

The above noted and other features of the invention will be better understood from the following detailed description when considered with reference to the accompanying drawings in which.

DETAILED DESCRIPTION

Figure 1:
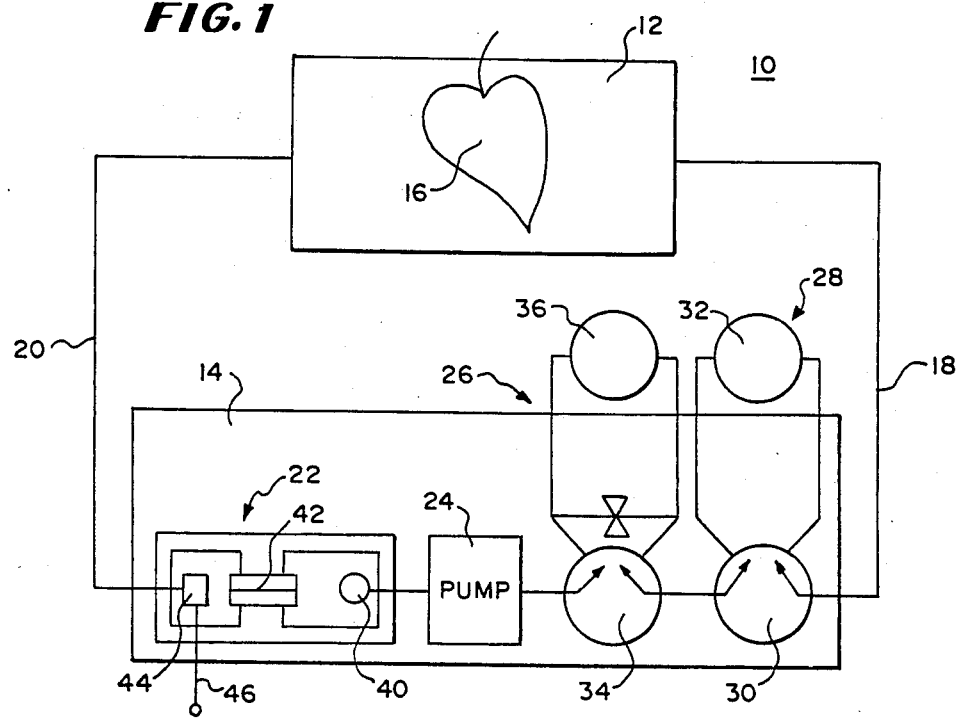
FIG. 1 is a schematic drawing of a photosynthesis analyzer in accordance with the invention.

In FIG. 1, there is shown a schematic view of a photosynthesis measuring instrument 10 having a plant chamber 12 and a gas analyzer 14, with a leaf 16 being within the plant chamber 12. The plant chamber 12 communicates with the gas analyzer 14 through conduits 18 and 20 to permit the flow of gas from the plant chamber 12 through the conduit 18 into the gas analyzer 14 and from the gas analyzer 14 back to the plant chamber 12 for the detection and measurement of photosynthesis in the leaf 16.

The plant chamber 12 is transparent and the entire photosynthesis measuring instrument 10 is adapted to be brought to the field so that a leaf or other part of a plant capable of photosynthesis may be placed in the enclosed container 12. While in the closed container, its gas transfer is analyzed to determine photosynthesis with the plant remaining in the field exposed to light. The plant chamber 12 is not part of this invention and is known to the prior art as a chamber for holding plant parts during analysis.

The gas analyzer 14 includes a carbon dioxide analyzer system 22, a pump 24, a desiccant system 26, and a carbon dioxide scrubber 28. These units are connected together and communicate with the interior of the plant chamber 12 through the conduits 18 and 20 so that gases are pumped from the chamber 12 through conduit 18, the carbon dioxide scrubber 28, the desiccant system 26, the pump 24, the carbon dioxide analyzer system 22 and back to the chamber 12 through conduit 20 in the order named. The carbon dioxide scrubber 28, the desiccant system 26, the pump 24, and the carbon dioxide analyzer system 22 are mounted in a housing roughly in the order described for easy connection one to the other.

To selectively remove carbon dioxide within the gas analyzer 14 for zeroing the photosynthesis measuring instrument, the carbon dioxide scrubber 28 includes a flow switch 30 which may be manually switched: (1) to pass the air directly to the desiccant system 26; or (2) to channel the air through a soda lime chamber 32 which removes carbon dioxide and thus obtain a zero reading from the carbon dioxide analyzer 22 for calibration.

To dry the air, the desiccant system 26 includes a flow switch 34 which may selectively cause the air to flow:: (1) through a desiccant chamber 36 in the same manner that it can selectively be channeled through a soda lime chamber 32 by the flow switch 30; or (2) directly through the pump 24 by-passing the desiccant chamber 36. The pump 24 draws air and pumps it through the carbon dioxide analyzer system 22.

To measure the amount of carbon dioxide, the carbon dioxide analyzer system 22 includes an infrared source 40, a flow cell 42, and a photosensor 44. The pump 24 pumps air through two channels of the flow cell 42 while the infrared source 40 shines light through the cells onto the photosensor 44, with light being transmitted through each of the channels in a manner to be described hereinafter. The amount of carbon dioxide is indicated by a signal from the photosensor on the conductor 46.

The photosynthesis system is not part of the invention itself except insofar as it cooperates with the infrared source 40 to provide a portable photosynthesis measuring instrument, which draws low power and can be used directly in the field. The infrared source 40 has other applications besides its use in the photosynthesis measuring instrument although in the preferred embodiment it is intended directly for such use or as an integral part of a stand alone carbon dioxide analyzer.

Figure 2:
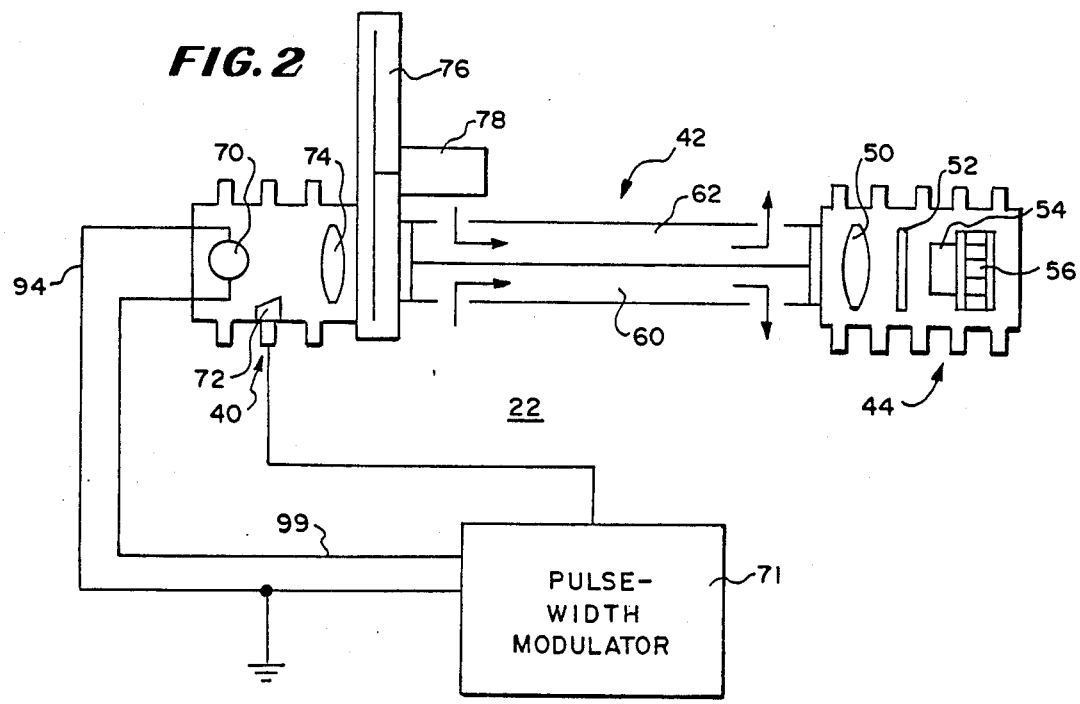
FIG. 2 is a schematic drawing of a carbon dioxide gas analyzer usable in the embodiment of FIG. 1.

In FIG. 2, there is shown a schematic diagram of the carbon dioxide analyzer 22 illustrating in greater detail the manner in which the infrared light source 40 transmits chopped light through two channels of the flow cell 42, each having a different carbon dioxide content, and to the photosensor 44 which measures the content. The flow cell 42 itself is not part of the invention but only the light emitting element within the infrared source 40 except insofar as the carbon dioxide analyzer 22 components cooperate with this light emitting element.

The photosensor 44 includes a lens 50, an optical filter 52, a detector 54 and a thermoelectric cooler 56 positioned in that order so that the light is picked up by the detector 54 after the desired frequency has been selected by the optical filter 52, with the lens 50 focusing the portion of the light that is intended to be received onto the active area of the detector 54. The output from the photosensor 44 is proportional to the difference between the absorbed light in the two channels of the flow cell 42.

The flow cell 42 contains a reference cell such as cell 60 and a sample cell such as 62 through which gas flows, with the reference cell having been purged of carbon dioxide. The light is transmitted directly though a longitudinal length of these cells in a manner known in the art.

The infrared light source 40 includes a light emitting unit 70, a pulse-width modulator 71, a feedback photodiode 72 and a lens 74. The pulse-width modulator 71 energizes the light source 40, providing more energy with a wider pulse and less power with a shorter width pulse. The feedback photodiode 72 receives light and feeds back a signal to control the flow of current through the light emitting unit 70 by controlling the width of the pulses from the pulse-width modulator 71. The lens 74 is a lens for focusing light from the light emitting unit 70 in a manner conventional in the art. A chopper 76 is driven by a motor 78 to chop the light for purposes of removing drift again in a conventional prior art manner.

Figure 3:
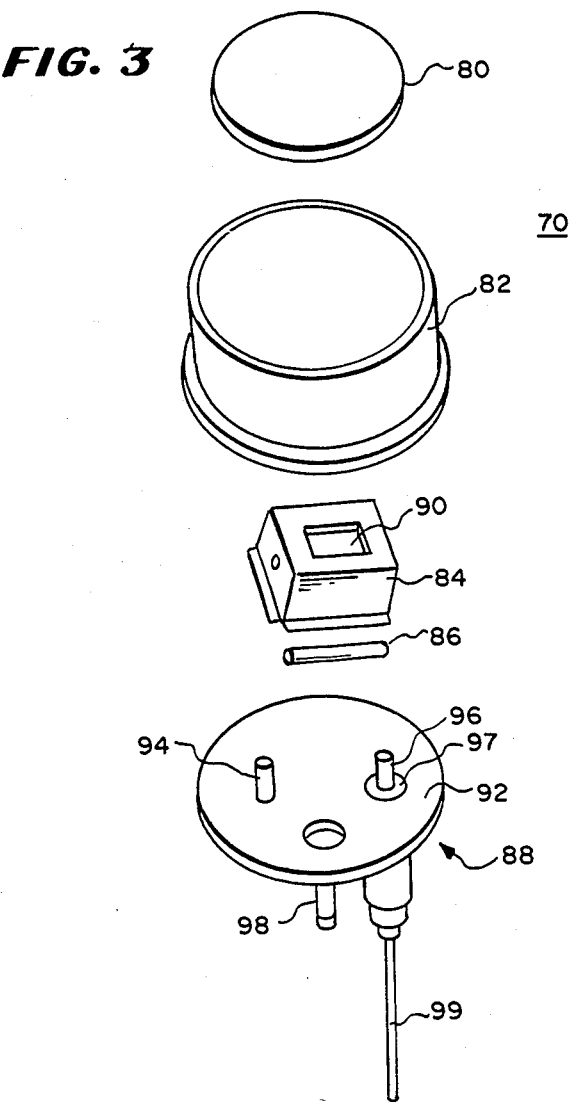
FIG. 3 is an exploded perspective view of an infrared light source usable in the embodiment of FIGS. 1 and 2.

In FIG. 3, there is shown an exploded perspective view of the light emitting unit 70 having a housing window 80, a housing 82, a reflector 84, an emitter-getter 86 and a base 88. The emitter-getter 86 fits within the reflector 84 and emits light through a window therein within the housing 82 and through the housing window 80. The base 88 seals the housing to maintain a vacuum therein.

The housing 82 has a diameter of approximately 2.5 centimeters and a height of approximately 11 millimeters. It has an open top adapted to be closed by the housing window 80 and a bottom adapted to be sealed by the base 88 to form an air tight compartment capable of sustaining a substantial vacuum at least equal to 70 grams per square centimeter.

The housing window 80 has a diameter sufficient to close the top of the housing 82 and, in the preferred embodiment, is approximately 2.5 centimeters, is cylindrical in shape and made of synthetic sapphire. It should: (1) be large enough to permit viewing a substantial portion of the emitter-getter surface 86; (2) be transparent to infrared light having a wavelength of 4.25 micrometers, attenuating such light by less than 15 percent; (3) transmit with low attenuation light within a 150 nanometer bandwidth and between light having wavelengths within the range of 4.1 micrometers to 4.4 micrometers; and (3) be strong enough to permit a vacuum within the housing 82 of at least a negative 70 grams per square centimeter.

The reflector 84 is generally box-shaped and has an interior surface reflective to heat. Its interior optics are designed to focus heat reflected by the reflective surface on a central axis within the reflector 84 along which central axis the emitter-getter 86 is mounted. This reflector design reduces the amount of radiation not utilized.

In the one surface of the reflector 84, there is an aperture 90 sufficiently large to expose a substantial portion of the emitter-getter 86 in an imaginary line leading between the photosensor 44 and light source 40 through the flow cell 42 (FIG. 1). This aperture has an area of at least 0.10 square millimeter and in the preferred embodiment is a 4 millimeters×4 millimeters square.

The interior surface of the reflector 84 should reflect at least 20 percent of the radiant heat not passing through the window 90 and the distance between at least 50 percent of the reflective walls and the closest point on the surface of the emitter-getter 86 is no greater than 1 centimeter. The reflective walls referred to in this paragraph are only the reflective walls shaped to focus heat onto the emitter-getter 86.

The emitter-getter 86 includes a material which is capable of serving as a non-evaporatable getter to maintain a vacuum and at the same time emit infrared radiation within a 150 nanometer bandwidth, which bandwidth encompasses 4.255 micrometer wavelength radiant energy and preferably which has 4.255 micrometer wavelength light as the center point of its high emission band.

The emitter-getter 86 is a cylinder mounted within the reflector 84 to have a portion of its surface exposed though the reflector window 90 within the aforementioned imaginary line through the window 90, the housing window 80, the flow cells 60 and 62 (FIG. 2) and the detector 54 (FIG. 2). It has within it a heater, which in the preferred embodiment is a tungsten heater electrically connected to conductors within the base 88 to permit its being heated.

The emitter-getter 86 is a porous mixture of a non-evaporatable getter material and a material which emits infrared light when heated. In the preferred embodiment, the getter material is zirconium and the light emitting material is carbon. It has a radient emissivity of 80 percent or, in other words, is an 80 percent black body and should be at least a 60 percent black body having a 60 percent emissivity. At least 50 percent of the surface is carbon.

In the preferred embodiment, the emitter-getter 86 is heated to 1,000 degrees kelvin and should be an emitter which emits infrared light when heated within the temperature range of 600 K. (Kelvin) to 2,000 K. The getter material is zirconium.

To heat the emitter-getter 86 and permit a vacuum to remain within the housing 82, the base 88 includes: (1) a flat base plate 92; (2) a ground electrode 94 electrically connected to the flat base plate 92 and extending upwardly to serve as a support for one end of the emitter-getter 86; and (3) a second electrode 96 extending through the base plate and electrically connected to an insulated power electrode 99, serving as a support for the other end of the emitter-getter 86.

An evacuation tubulation 98 extends through the base and is closed at its other end after the cell has been evacuated by a vacuum pump. The power electrode 94 and second electrode 96 is insulated from the conductive base plate 92 by an insulative ring 97 therein and are adapted to be electrically connected to the pulse-width modulator 71 (FIG. 2) through a conductor 99 (FIGS. 2 and 3).

With this arrangement, the electrodes 94 and 96 support the emitter-getter 86 within the reflector 84 and at the same time permit an AC potential to be applied through it to heat it to approximately 1,000 degrees K. The arrangement causes: (1) conservation of energy by reflection of heat from closely adjacent surfaces; (2) a large-volume vacuum to permit dispersion of gas that escapes into the vacuum; (3) ease of sealing the chamber because of its convenient size; and (4) gettering action in intimate contact with the radiating surfaces, which provides unexpectedly long life.

Figure 4:
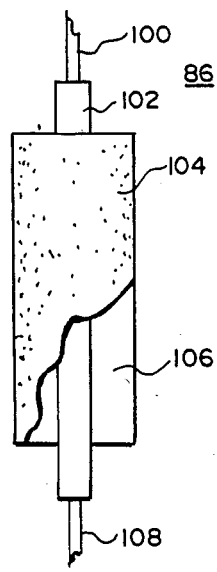
FIG. 4 is an elevational view, partly broken away, of an efficient combined getter and radiation emitter usable in the embodiments of FIGS. 1-3.

In FIG. 4, there is shown an elevational view, partly broken away of the emitter-getter 86 having conductive leads 100 and 108, an internal heater 102, a carbon outer coat 104 and an interior porous body of combined; (1) infrared-light emitting material; and (2) getter material 106. In the preferred embodiment, the internal heater 102 is a cylindrical tungsten heating element having a resistance at least 5 times that of the leads to cause most of the heat created by the flow of electricity though it to be created within the center of the emitter-getter 86.

The emitter-getter 86 includes, adjacent to the heater 102, a cylindrical porous mass of emitter material and getter material which, in the preferred embodiment, is sintered zirconium and carbon. The outer coat is cylindrical and is a porous layer of spectrographic carbon rubbed on to the body so that the outer surface is at least 50 percent new graphite. The getter is activated in a manner known in the art and the heater is within the infrared source to permit the efficient use of power to heat the carbon into an efficient infrared radiator while at the same time permitting gettering action to take place within a small space.

To make said emitter-getter 86, a cylindrical zirconium-carbon getter is obtained. Such getters are known in the art and manufactured by sintering together zirconium powder or other non-evaporable getter material with carbon to form a highly porous combination. In the preferred embodiment, this combination is formed around a cylindrical tungsten heater. Getters of this type may be purchased from SAES GETTERS S.p.A. VIA Gallarate 215, 1-20151 Milano, Italy. The particular model found useful is designated St 171/LH1/4-7/200.

This getter is improved in its emissivity to an emissivity of at least 60 percent by rubbing further carbon along its surface with a spectrographic rod until the surface appears substantially coated. It should be coated on at least 50 percent of its surface and yet should remain porous to gas.

In the preferred embodiment, the emitter-getter 86 is coated until it has an 80 percent emissivity. The wire conductor leads that are connected to the central tungsten heater have a diameter of 0.2 millimeters and the cylindrical adjacent sintered mass of zirconium and carbon has: (1) a diameter of approximately 4 millimeters; and (2) a cylindrical length of approximately 7.2 millimeters.

The getter material in the emitted getter 86 is activated in a manner known in the art by heating it for a short period of time in a vacuum. After being formed, it is mounted in a cell having a synthetic sapphire window and capable of supporting a high vacuum. The leads to the emitter-getter 86 are mounted to electrodes within the cell, with both electrodes either extending out of the cell for electrical energization or one of the electrodes being grounded and the other extending through the cell for energization.

In use, the electrodes are energized by a pulse-width modulator and the light emitted is received and used to control the width of the pulses to maintain the temperature of the emitter-getter 86 at approximately 1,000 K. The light is emitted and shines through the window in the reflector 84 while the reflector 84 reflects heat back onto the surface of the emitter-getter 86. The light is focused through a chopper to reduce DC drift in the electronics of the circuit and transmitted through flow cells to detect carbon dioxide. It is received by a photocell to indicate the amount of carbon dioxide in the carbon dioxide analyzer 22.

From the above description, it can be understood that the carbon dioxide analyzer and the infrared source of this invention have several advantages such as: (1) they have high emissivity in the infrared region; (2) they have low power consumption; (3) the heat utilized in gettering activity is also utilized to efficiently convert electricity to infrared radiation; (4) the unit is compact; (5) a relatively strong mechanical support is combined with a high emissivity material which by itself is not mechanically strong to create a mechanically strong, high infrared emissivity source; and (6) a combined getter and high emissivity source is provided which functions in a superior manner as an infrared emitter compared to other infrared emitters without a getter and infrared emitters with a separate getter.

Although a preferred embodiment of the invention has been described with some particularity, many modifications and variations in the preferred embodiment are possible in light of the above teachings. Therefore, it is to be understood that, within the scope of the appended claims, the invention may be practiced other than as specifically described.

What is claimed is:

1. A carbon dioxide analyzer comprising:
   a source of infrared light;
   a flow cell adapted to contain a gas;
   a detector for converting infrared radiation to electrical signals; and
   said source of infrared light including combined means energized from a single source for serving as a getter and an emitter of infrared light.

2. A carbon dioxide analyzer in accordance with claim 1 in which said source of infrared light is within a vacuum.

3. A carbon dioxide analyzer in accordance with claim 2 in which said combined means energized from a single source for emitting infrared light and serving as a getter includes infrared light emitting portions and getter portions not spaced from each other by a distance greater than 1 nanometer.

4. A carbon dioxide analyzer according to claim 3 in which said source of infrared light emits light in a strong spectrum including light having a wavelength of 4.2 micrometers.

5. A carbon dioxide analyzer in accordance with claim 4 in which said source of infrared light emits lights having a bandwidth of at least 150 nanometers.

6. A carbon dioxide analyzer in accordance with claim 5 in which said source of infrared light includes means for emitting light having a bandwidth of at least 150 nanometers with a center point of substantially 4.2 micrometers.

7. A carbon dioxide analyzer in accordance with claim 6 in which:
   said combined means energized from a single source for serving as a getter and as an emitter of infrared light includes reflective means located within a range of no more than 1 centimeter from said means for emitting infrared radiation for reflecting heat back to said means for emitting infrared radiation from at least 50 percent of its surface; and
   said reflector having a window aligned with said infrared light detector with an opening of area of between 0.05 to 20 square millimeters.

8. A carbon dioxide analyzer in accordance with claim 7 having means for heating said source of infrared radiation to a temperature in the range of 600 K. to 2,000 K.

9. A carbon dioxide analyzer in accordance with claim 8 in which said source of infrared radiation includes a sintered together getter material and infrared emitting material.

10. A carbon dioxide analyzer in accordance with claim 9 in which:
    said source of infrared radiation includes spectrographic grade carbon covering at least 60 percent of its outer surface; and
    said combined means including said spectrographic grade carbon being gas porous.

11. A carbon dioxide analyzer in accordance with claim 1 in which said combined means energized from a single source for emitting infrared light and serving as a getter includes infrared light emitting portions and getter portions not spaced from each other by a distance greater than 1 nanometer.

12. A carbon dioxide analyzer according to claim 11 in which said source of infrared light emits light in a strong spectrum including light having a wavelength of 4.2 micrometers.

13. A carbon dioxide analyzer in accordance with claim 12 in which said source of infrared light emits lights having a bandwidth of at least 150 nanometers.

14. A carbon dioxide analyzer in accordance with claim 13 in which said source of infrared light includes a means for emitting light having a bandwidth of at least 150 nanometers with a center point of substantially 4.2 micrometers.

15. A carbon dioxide analyzer in accordance with claim 14 in which:
    said combined means energized from a single source for serving as a getter and as an emitter of infrared light includes reflective means located within a range of no more than 1 centimeter from said means for emitting infrared radiation for reflecting heat back to said means for emitting infrared radiation from at least 50 percent of its surface; and said reflector having a window aligned with said infrared light detector with an opening of area of between 0.05 to 20 square millimeters.

16. A carbon dioxide analyzer in accordance with claim 15 having means for heating said source of infrared radiation to a temperature in the range of 600 K. to 2,000 K.

17. A carbon dioxide analyzer in accordance with claim 16 in which said source of infrared radiation includes a sintered together getter material and infrared emitting material.

18. A carbon dioxide analyzer in accordance with claim 17 in which:
   said source of infrared radiation includes spectrographic grade carbon covering at least 60 percent of its outer surface; and
   said combined means including said spectrographic grade carbon being gas porous.

19. A carbon dioxide analyzer according to claim 1 in which said source of infrared light emits light in a strong spectrum including light having a wavelength of 4.2 micrometers.

20. A carbon dioxide analyzer in accordance with claim 19 in which said source of infrared light emits lights having a bandwidth of at least 150 nanometers.

21. A carbon dioxide analyzer in accordance with claim 20 in which said source of infrared light includes means for emitting light having a bandwidth of at least 150 nanometers with a center point of substantially 4.2 micrometers.

22. A carbon dioxide analyzer in accordance with claim 21 in which:
   said combined means energized from a single source for serving as a getter and as an emitter of infrared light includes reflective means located within a range of no more than 1 centimeter from said means for emitting infrared radiation for reflecting heat back to said means for emitting infrared radiation from at least 50 percent of its surface; and
   said reflector having a window aligned with said infrared light detector with an opening of area of between 0.05 to 20 square millimeters.

23. A carbon dioxide analyzer in accordance with claim 22 having means for heating said source of infrared radiation to a temperature in the range of 600 K. to 2,000 K.

24. A carbon dioxide analyzer in accordance with claim 23 in which said source of infrared radiation includes a sintered together getter material and infrared emitting material.

25. A carbon dioxide analyzer in accordance with claim 24 in which:
   said source of infrared radiation includes spectrographic grade carbon covering at least 60 percent of its outer surface; and
   said combined means including said spectrographic grade carbon being gas porous.

26. A carbon dioxide analyzer in accordance with claim 1 in which said source of infrared light emits lights having a bandwidth of at least 150 nanometers.

27. A carbon dioxide analyzer in accordance with claim 26 in which said source of infrared light includes means for emitting light having a bandwidth of at least 150 nanometers with a center point of substantially 4.2 micrometers.

28. A carbon dioxide analyzer in accordance with claim 27 in which:
   said combined means energized from a single source for serving as a getter and as an emitter of infrared light includes reflective means located within a range of no more than 1 centimeter from said means for emitting infrared radiation for reflecting heat back to said means for emitting infrared radiation from at least 50 percent of its surface; and
   said reflector having a window aligned with said infrared light detector with an opening of area of between 0.05 to 20 square millimeters.

29. A carbon dioxide analyzer in accordance with claim 28 having means for heating said source of infrared radiation to a temperature in the range of 600 K. to 2,000 K.

30. A carbon dioxide analyzer in accordance with claim 29 in which said source of infrared radiation includes a sintered together getter material and infrared emitting material.

31. A carbon dioxide analyzer in accordance with claim 30 in which:
   said source of infrared radiation includes spectrographic grade carbon covering at least 60 percent of its outer surface; and
   said combined means including said spectrographic grade carbon being gas porous.

32. A carbon dioxide analyzer in accordance with claim 1 in which said source of infrared light includes means for emitting light having a bandwidth of at least 150 nanometers with a center point of substantially 4.2 micrometers.

33. A carbon dioxide analyzer in accordance with claim 32 in which:
   said combined means energized from a single source for serving as a getter and as an emitter of infrared light includes reflective means located within a range of no more than 1 centimeter from said means for emitting infrared radiation for reflecting heat back to said means for emitting infrared radiation from at least 50 percent of its surface; and
   said reflector having a window aligned with said infrared light detector with an opening of area of between 0.05 to 20 square millimeters.

34. A carbon dioxide analyzer in accordance with claim 33 having means for heating said source of infrared radiation to a temperature in the range of 600 K. to 2,000 K.

35. A carbon dioxide analyzer in accordance with claim 34 in which said source of infrared radiation includes a sintered together getter material and infrared emitting material.

36. A carbon dioxide analyzer in accordance with claim 35 in which:
   said source of infrared radiation includes spectrographic grade carbon covering at least 60 percent of its outer surface; and
   said combined means including said spectrographic grade carbon being gas porous.

37. A carbon dioxide analyzer in accordance with claim 1 in which:
   said combined means energized from a single source for serving as a getter and as an emitter of infrared light includes reflective means located within a range of no more than 1 centimeter from said means for emitting infrared radiation for reflecting heat back to said means for emitting infrared radiation from at least 50 percent of its surface; and said reflector having a window aligned with said infrared light detector with an opening of area of between 0.05 to 20 square millimeters.

38. A carbon dioxide analyzer in accordance with claim 37 having means for heating said source of infrared radiation to a temperature in the range of 600 K. to 2,000 K.

39. A carbon dioxide analyzer in accordance with claim 38 in which said source of infrared radiation includes a sintered together getter material and infrared emitting material.

40. A carbon dioxide analyzer in accordance with claim 39 in which:

said source of infrared radiation includes spectrographic grade carbon covering at least 60 percent of its outer surface; and said combined means including said spectrographic grade carbon being gas porous.

41. A carbon dioxide analyzer in accordance with claim 1 having means for heating said source of infrared radiation to a temperature in the range of 600 K. to 2,000 K.

42. A carbon dioxide analyzer in accordance with claim 41 in which said source of infrared radiation includes a sintered together getter material and infrared emitting material.

43. A carbon dioxide analyzer in accordance with claim 42 in which:

said source of infrared radiation includes spectrographic grade carbon covering at least 60 percent of its outer surface; and said combined means including said spectrographic grade carbon being gas porous.

44. A carbon dioxide analyzer in accordance with claim 1 in which said source of infrared radiation includes a sintered together getter material and infrared emitting material.

45. A carbon dioxide analyzer in accordance with claim 44 in which:

said source of infrared radiation includes spectrographic grade carbon covering at least 60 percent of its outer surface; and said combined means including said spectrographic grade carbon being gas porous.

46. A carbon dioxide analyzer in accordance with claim 1 in which:

said source of infrared radiation includes spectrographic grade carbon covering at least 60 percent of its outer surface; and said combined means including said spectrographic grade carbon being gas porous.

47. A method of generating infrared radiation comprising the steps of:

applying electrical energy through a heater within a mass of sintered getter material and high emissivity material until the temperature of said material reaches a point at which the getter material operates efficiently without vaporization and the high emissivity material emits infrared radiation; and transmitting said radiation through a filter to select a range of frequencies, whereby infrared radiation within a selected range of frequencies is supplied.

48. A method in accordance with claim 47 in which said step of transmitting said radiation through a filter includes the step of selecting frequencies within a waveband of 150 nanometers.

49. A method according to claim 48 in which the step of transmitting said radiation through a filter includes the step of selecting a frequency within a band of at least 150 nanometers having within said band light of a wavelength of 4.2 microns.

50. A method according to claim 47 in which the step of transmitting said radiation through a filter includes the step of selecting a frequency within a band of at least 150 nanometers having within said band light of a wavelength of 4.2 microns.

51. A source of infrared radiation comprising:

a heater;

combined means in intimate contact with said heater for serving as both a getter and as an emitter of infrared radiation when heated by said heater;

said heater and combined means being mounted in a vacuum;

said combined means including powdered zirconium and carbon sintered together; and said source of infrared radiation further including a coat of spectrographic carbon over at least 50 percent of the surface of said combined means.

52. A source of infrared radiation according to claim 51 further including reflector means spaced from said combined means for reflecting heat back to said combined means.

53. A source of infrared radiation according to claim 52 in which said heater is an electrical heater and said combined means is formed at least partly about said heater.

54. A source of infrared radiation according to claim 53 further including means for causing said heater to increase the temperature of said combined means to a temperature of between 600 K. and 2,000 K.

55. A source of infrared radiation comprising:

a heater;

combined means in intimate contact with said heater for serving as both a getter and as an emitter of infrared radiation when heated by said heater;

said combined means including powdered zirconium and carbon sintered together;

said source of infrared radiation further including a coat of spectrographic carbon over at least 50 percent of the surface of said combined means.

56. A source of infrared radiation according to claim 55 further including reflector means spaced from said combined means for reflecting heat back to said combined means.

57. A source of infrared radiation according to claim 56 in which said heater is an electrical heater and said combined means is formed at least partly about said heater.

58. A source of infrared radiation according to claim 57 further including means for causing said heater to increase the temperature of said combined means to a temperature of between 600 K. and 2,000 K.

59. A source of infrared radiation comprising:

a heater;

combined means in intimate contact with said heater for serving as both a getter and as an emitter of infrared radiation when heated by said heater;

said source of infrared radiation further including a coat of spectrographic carbon over at least 50 percent of the surface of said combined means.

60. A source of infrared radiation according to claim 59 further including reflector means spaced from said combined means for reflecting heat back to said combined means.

61. A source of infrared radiation according to claim 60 in which said heater is an electrical heater and said combined means is formed at least partly about said heater.

62. A source of infrared radiation according to claim 61 further including means for causing said heater to increase the temperature of said combined means to a temperature of between 600 K. and 2,000 K.

63. A source of infrared radiation comprising:
a heater;
combined means in intimate contact with said heater for serving as both a getter and as an emitter of infrared radiation when heated by said heater;
said source of infrared radiation further including reflector means spaced from said combined means for reflecting heat back to said combined means.

64. A source of infrared radiation according to claim 63 in which said heater is an electrical heater and said combined means is formed at least partly about said heater.

65. A source of infrared radiation according to claim 64 further including means for causing said heater to increase the temperature of said combined means to a temperature of between 600 K. and 2,000 K.

66. A method of making an infrared light source comprising the steps of:
sintering carbon and a getter material about a heater;
coating the sintered mass with further carbon until at least 50 percent of the surface is carbon while maintaining porosity of the sintered material; and
mounting said body within a vacuum.

67. A method according to claim 66 in which the step of sintering together a getter material and carbon includes the step of singering together zirconium and carbon.

68. An infrared light emitting unit comprising:
a gas tight housing having within it a vacuum;
said gas tight housing containing a single source of infrared radiation;
said single source of infrared radiation including a heater and combined means for serving as both a getter and as an emitter of infrared radiation when heated by said heater.

69. An infrared source comprising:
a heater;
combined means in intimate contact with said heater for serving as both a getter and as an emitter of infrared radiation when heated by said heater;
said combined means including means for providing infrared radiation with at least 60 percent emissivity covering at least 50 percent of the surface of said combined means.

70. An infrared source according to claim 69 in which said means for providing infrared radiation with at least 60 percent emmissivity includes a coat of spectrographic carbon.

71. An infrared source according to claim 70 in which said means for providing infrared radiation with at least 60 percent emmissivity includes reflector means spaced from said combined means for reflecting heat back to said combined means.

72. An infrared source according to claim 71 in which said heater is an electrical heater and said combined means is formed at least partly about said heater.

* * * * *